US009636119B2

(12) United States Patent
Jacobs

(10) Patent No.: US 9,636,119 B2
(45) Date of Patent: May 2, 2017

(54) SURGICAL CUTTING TOOL

(71) Applicant: DePuy Synthes Products, Inc., Raynham, MA (US)

(72) Inventor: Scott Jacobs, Honey Brook, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 14/919,125

(22) Filed: Oct. 21, 2015

(65) Prior Publication Data

US 2016/0038156 A1 Feb. 11, 2016

Related U.S. Application Data

(62) Division of application No. 13/693,426, filed on Dec. 4, 2012, now Pat. No. 9,198,671.

(51) Int. Cl.
*A61B 17/14* (2006.01)
*A61B 17/16* (2006.01)
*A61B 17/32* (2006.01)

(52) U.S. Cl.
CPC .......... *A61B 17/14* (2013.01); *A61B 17/1608* (2013.01); *A61B 17/32002* (2013.01); *A61B 2017/32006* (2013.01); *A61B 2017/320008* (2013.01); *A61B 2017/320028* (2013.01)

(58) Field of Classification Search
CPC .............. A61B 17/148; A61B 17/1608; A61B 17/1606
USPC ...................................... 606/79–85
See application file for complete search history.

(56) References Cited

U.S. PATENT DOCUMENTS

| | | | |
|---|---|---|---|
| D324,424 S | | 3/1992 | Michelson |
| 5,340,360 A | * | 8/1994 | Stefanchik ......... A61B 17/1285 227/901 |
| 5,681,314 A | * | 10/1997 | Derouin .............. A61B 17/158 606/79 |
| 5,697,889 A | | 12/1997 | Slotman et al. |
| 6,139,560 A | | 10/2000 | Kremer |
| 7,749,228 B2 | | 7/2010 | Lieberman |
| 7,947,044 B2 | | 5/2011 | Ullrich, Jr. et al. |
| 2005/0033338 A1 | | 2/2005 | Ferree |
| 2006/0089649 A1 | | 4/2006 | Ullrich, Jr. et al. |
| 2008/0161809 A1 | * | 7/2008 | Schmitz ............. A61B 17/1604 606/79 |

(Continued)

FOREIGN PATENT DOCUMENTS

WO WO 2004/060175 7/2004

OTHER PUBLICATIONS

Bridwell, Keith, et al., *Pedicle Subtraction Osteotomy for the Treatment of Fixed Sagittal Imbalance*, The Journal of Bone and Joint Surgery, Mar. 2003, vol. 85-A, pp. 454-463.

(Continued)

*Primary Examiner* — Christopher Beccia
(74) *Attorney, Agent, or Firm* — Raymond N. Scott, Jr.

(57) ABSTRACT

A surgical cutting tool including a first jaw and a second jaw operably associate with the first jaw such that the first jaw and the second jaw are movable relative to one another between an opened position and a closed position. A cutting member is movably attached to the first jaw so that the cutting member extends from the first jaw towards the second jaw, and an actuating mechanism is operably associated with the cutting member so as to cause the cutting member to move relative to the first jaw.

7 Claims, 10 Drawing Sheets

(56) References Cited

U.S. PATENT DOCUMENTS

2008/0221383 A1\* 9/2008 Way ................. A61B 17/295
  600/3
2011/0184465 A1  7/2011 Boehm
2011/0224672 A1  9/2011 Ullrich, Jr. et al.

OTHER PUBLICATIONS

Bridwell, Keith, et al., *Pedicle Subtraction Osteotomy for the Treatment of Fixed Sagittal Imbalance, Surgical Technique*, The Journal of Bone and Joint Surgery, Mar. 2004, vol. 86-A, pp. 44-50.

\* cited by examiner

SURGICAL CUTTING TOOL

CROSS-REFERENCE TO RELATED APPLICATIONS

This application is a divisional of U.S. application Ser. No. 13/693,426, filed Dec. 4, 2012, the disclosure of which are hereby incorporated by reference as if set forth in their entirety herein.

BACKGROUND

1. Field of the Inventive Concepts

The concepts disclosed herein are generally related to surgical devices, and more particularly, but not by way of limitation, to a surgical cutting tool and methods of using same.

2. Brief Description of Related Art

The human spine is a highly complex bone and connective tissue structure which includes over twenty vertebral bones coupled to one another so as to house and protect critical elements of the nervous system. In addition, the spine is a highly flexible structure, capable of a high degree of curvature and twist in multiple directions. The vertebral bones and connective tissue of a human spine are coupled sequentially to one another by a tri joint complex which consists of an anterior disc joint and the two posterior facet joints. The anterior discs of adjacent vertebral bones are separated and cushioned by cartilage spacers referred to as intervertebral discs. The vertebral bones of the spine are classified as cervical, thoracic, lumbar, and sacral.

The cervical portion of the spine, which comprises the upper portion of the spine up to the base of the skull, is the most flexible of all the regions of the spine, and includes the first seven vertebrae. The twelve intermediate bones comprise the thoracic vertebrae, and connect to the lower spine which comprises the five lumbar vertebrae. The base of the spine is the sacral bones (including the coccyx).

A typical human vertebral bone consists of two essential parts: an anterior (front) segment, which is the vertebral body; and a posterior part—the vertebral (neural) arch—which encloses the vertebral foramen. The vertebral arch is formed by a pair of pedicles and a pair of laminae, and supports seven processes—four articular, two transverse, and one spinous.

The healthy adult human spine is generally S-shaped, having a lordotic curvature in the lumbar region and a kyphotic curvature in the thoracic portion and cervical portion. The lordotic curvature and the kyphotic curvature typically balance out in a healthy human spine, such that the healthy human spine has an overall vertical shape and overall approximately neutral curvature.

However, some disease processes or injuries may cause and excessive lumbar curvature known as lordosis, or an excessive thoracic curvature know as kyphosis in some patients. In some cases of spinal degenerative disease, developmental problems, or trauma, the alignment of the spine may become severely compromised, which may result in excess kyphosis, in some severe cease rendering the patient unable to carry on the normal activities of daily life, and subjecting them to significant pain and limited mobility.

Fortunately, several surgical procedures have been developed, to decrease the kyphotic curvature, increase the lordotic curvature, or combinations thereof, to return the spine closer to its healthy natural alignment.

One such surgical procedure, commonly known as a pedicle subtraction osteotomy (PSO), has been developed to correct the alignment of the spinal column such that the height of the spine is not significantly compromised, and such that the spine is realigned to approximate the natural curvature of the spine.

PSO is generally performed via a posterior access (e.g., through the back) to the spine, and involves removing all posterior features of one or more vertebrae, including the pedicles. Next, cancellous bone is removed from the vertebral body via two openings located at the former pedicle bases positioned on both sides of the spinal cord from the vertebral body such that a generally V-shaped longitudinal notch (relative to the spine) is formed in the vertebral body. Due to the proximate location of the spinal cord and adjacent nerve roots, a "bone bridge" (a posterior portion of the vertebral body which cannot be removed due to its location under the spinal cord) remains under the spinal cord and extends between the two openings. A portion of a ligament known as the posterior longitudinal ligament (PLL) may also extend over the bone bridge, between the bone bridge and the spinal column, in some cases.

To remove this bone bridge or the associated portion of the PLL, one or more surgical cutting tools are used, such as elevators to lift and move away the spinal cord and adjacent nerve roots, and one or more curettes, which may be manually pushed in or tapped with a surgical hammer to gradually cut, or chip, through the bone bridge or the PLL. Next, other suitable surgical cutting tools may be used to extract any cut-away portions of the bone bridge or PLL, while moving the spinal cord and adjacent nerve roots out of the way with an elevator.

After the bone bridge and PLL are cut away and extracted or removed from the vertebral body, the lateral wall portions of the vertebral body are similarly cut away so that the V-shaped notched formed in the vertebral body may be collapsed onto itself to re-shape the vertebral body into a wedge shape. The changed shape of the vertebral body may result in a change of the angle of the spine by increasing its lordotic curvature. The PSO procedure may be carried out on one or more vertebral bodies, as indicated in a particular case.

Supplemental support mechanisms, such as spinal support rods or plates, and appropriate fixation points along the spine, may then be used to secure the spine in any desired position and curvature such that a compressive force is maintained on the cut vertebral body or bodies, to facilitate the healing of the cut vertebral body, such that the cut may heal.

The removal of the bone bridge and the PLL from the posterior end of the vertebral body is a part of the PSO procedure that is prone to error and is highly dependent on surgeon skill and local patient anatomy. For example, curettes or other surgical cutting tools that may be used to cut the bone bridge and the PLL behave differently when encountering bone tissue versus encountering the PLL. Impinging or pushing against bone tissue with a curette produces little or no rebound of the curette, and impinging or pushing against the PLL with a curette may result in rebound of the curette, which may cause the curette to slip or move off-target. Further, the elevator or other surgical cutting tool used to lift the spinal column and adjacent nerve roots to move them out of the way may cause unintentional injury to such tissues. Additionally, the tight spaces and the proximity of the spinal cord and the adjacent nerve roots may result in neurological injuries or damage in some cases, where the curette, elevator, or other surgical cutting tool slip or otherwise become dislodged or displaced during the removal of the bone bridge and encounters the spinal cord or an adjacent nerve root.

Further, the force applied by the curette may cause the bone bridge to break up into one or more bone fragments which may have sharp edges and which may move or deflect in various directions after breaking off from the vertebrae. Deflection or movement of such sharp bone fragments is typically carefully controlled during the procedure, and the fragments are accounted for and carefully extracted from the surgical site, to avoid injuring adjacent nervous tissues and potential post-operative complications. However, the unpredictable deflection of bone fragments, as well as the number and size of fragments can vary significantly during each procedure, and the control and removal of such fragments are highly dependent on surgeon skill and patient anatomy, and add undesired complexity and time to the procedure.

Besides a PSO, other surgical procedures may be performed that involve cutting of bone or other tissue in locations where injuries to adjacent tissues are of concern, or where careful control of the resulting bone or other tissue fragments is desired.

DETAILED DESCRIPTION OF EXEMPLARY EMBODIMENTS

Figure 1:
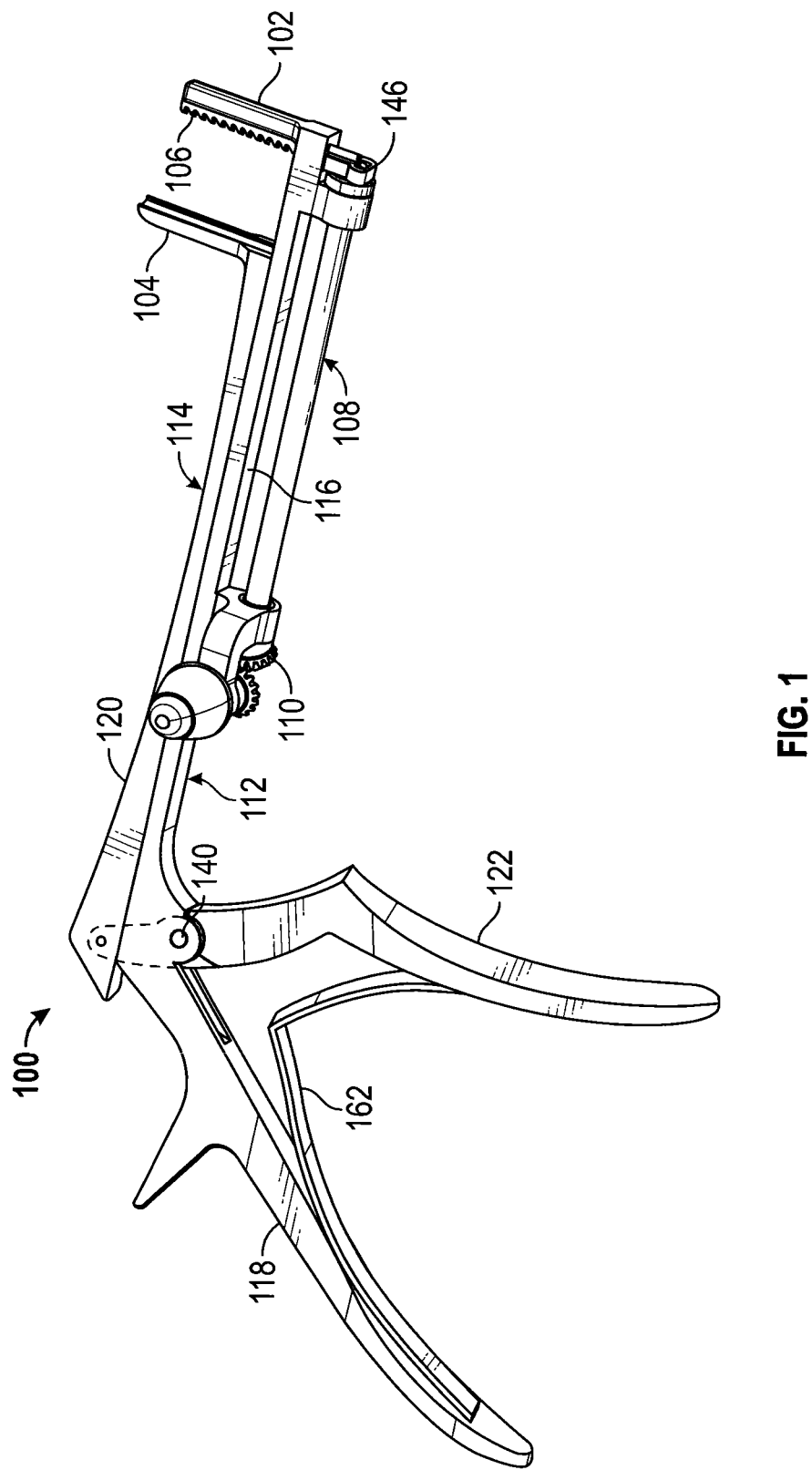
FIG. 1 is a perspective view of an exemplary embodiment of a surgical cutting tool constructed in accordance with the inventive concepts disclosed herein.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

As is known by persons of ordinary skill in the art, established human anatomical orientation designations are used to avoid ambiguities when referring to a body part relative to another body part. A standard anatomical position (i.e., standing upright facing forward with arms to the side, palms facing forward, thumbs pointing laterally away from the body) has been established, and such orientation designations refer to the various body parts in the standard position, without regard to their actual position. For the purposes of the instant disclosure such standard human anatomy terminology may be used to describe the various orientation and interrelationships of the different parts of a user's body. For example, the terms "anterior," "posterior," "superior," "inferior," "lateral," "medial," and related terms or phrases designate relative positions and orientations in the patient's body to which reference is made and are not meant to be limiting. Further, the terms "left," "right," "lower," "upper," "top," and "bottom" may designate general directions in the drawings to which reference is made, for example, and are not meant to be limiting. The terms "inner," "inwardly," or "distally," and "outer," "outwardly," or "proximally" may refer to directions toward or away from the geometric center of the device and related parts thereof, or the patient's body, for example, and are not intended to be limiting.

As used herein, the term "patient" is not limited to a human being, and is intended to include all organisms, whether alive or dead, including any species having soft tissues and bones. For example, adjustable endplates according to the instant disclosure may be used in a human, horse, cow, sheep, cat, dog, and the like. In another example, surgical cutting tools and methods according to the instant disclosure may be used in a non-living organism or in an artificial anatomical model to train medical or veterinary personnel in surgical techniques. Further, virtual representations of surgical cutting tools and methods according to the instant disclosure may be used in a virtual simulation to train medical or veterinary personnel in surgical techniques, for example.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 2:
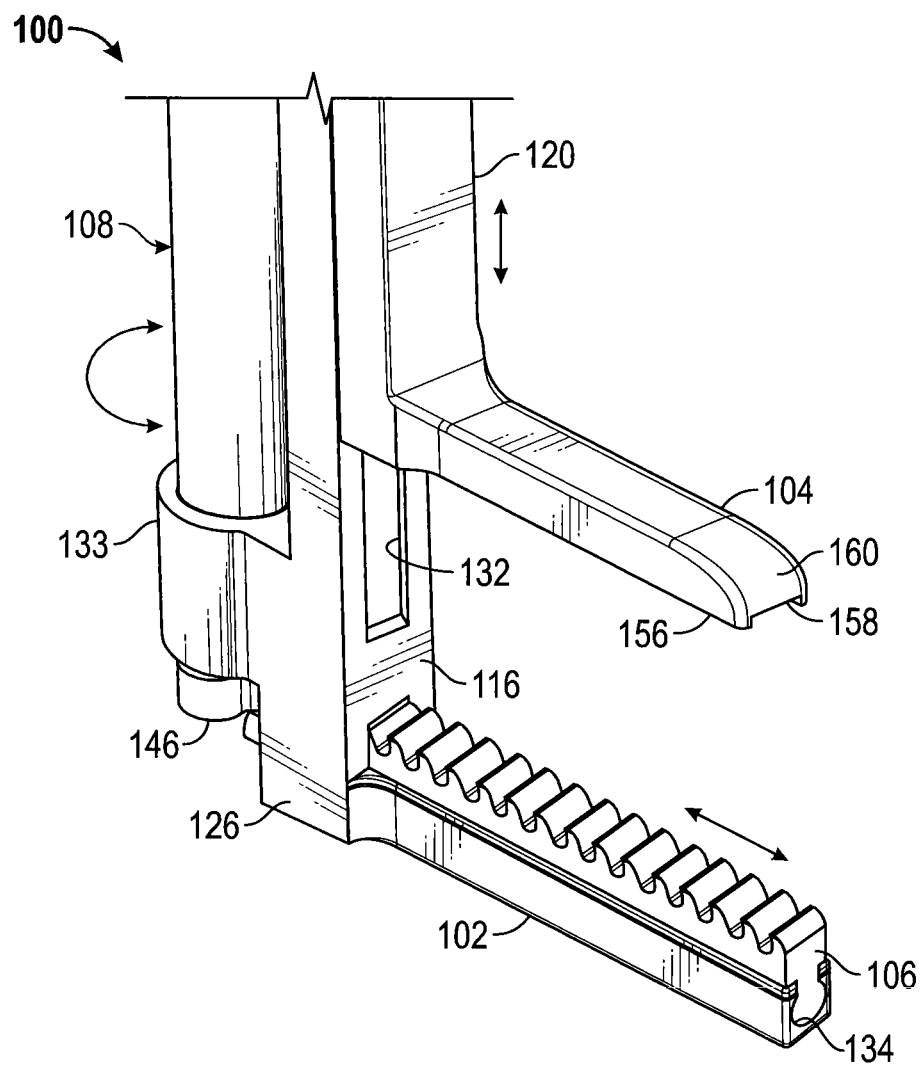
FIG. 2 is an enlarged, perspective view of the surgical cutting tool in an opened position.
Figure 11:
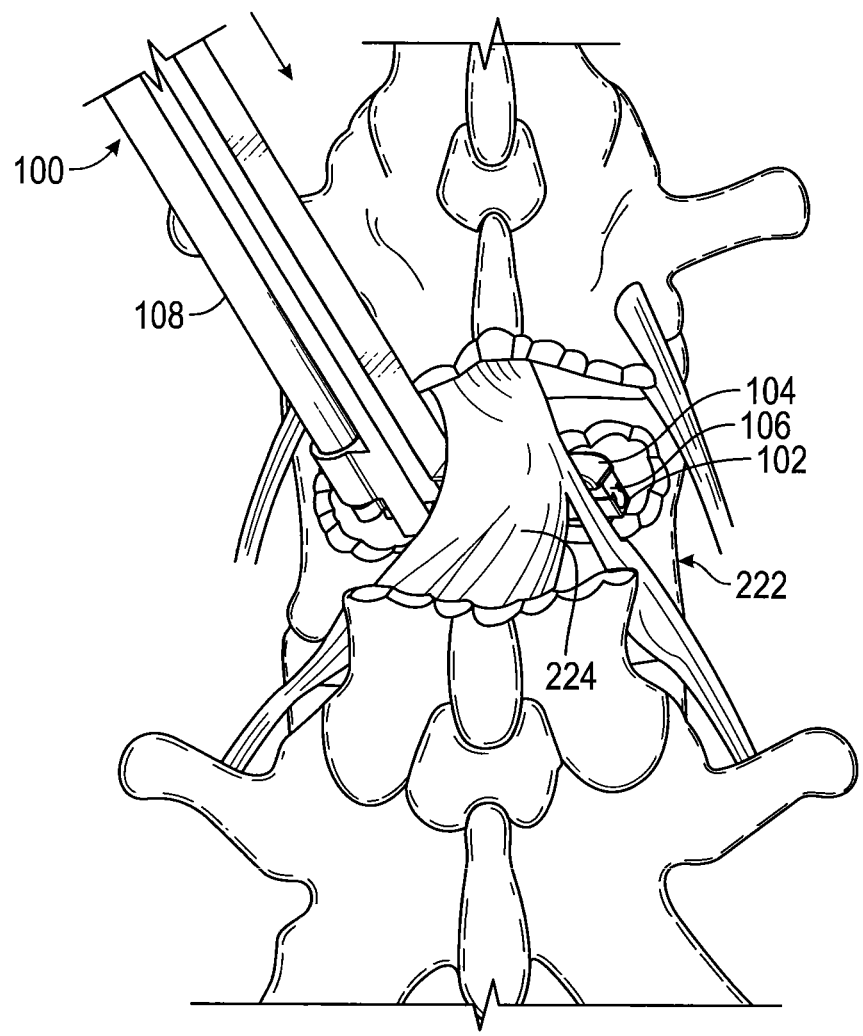
Figure 12:
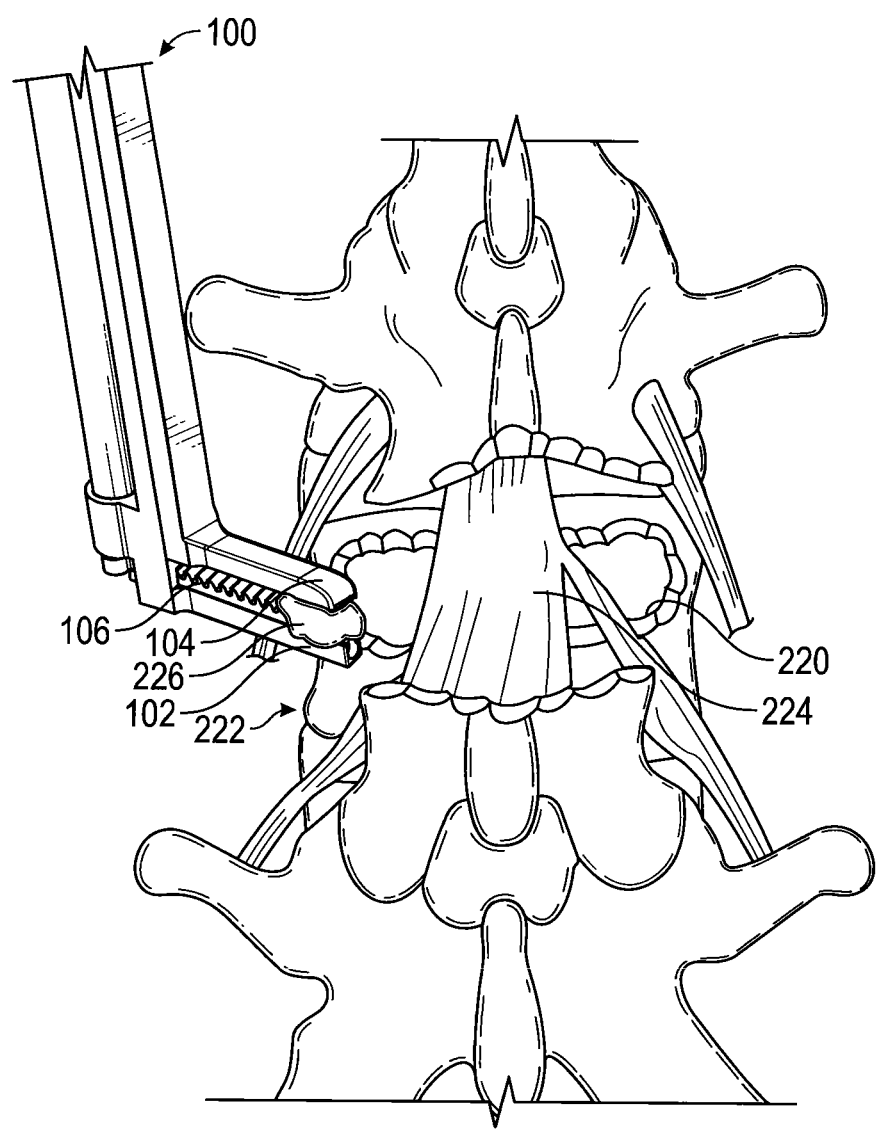

Referring now to FIGS. 1 and 2, one embodiment of a surgical cutting tool 100 constructed in accordance with the inventive concepts disclosed herein is illustrated. Broadly, the surgical cutting tool 100 includes a first jaw 102 and a second jaw 104 operably associate with the first jaw 102 such that the first jaw 102 and the second jaw 104 are movable relative to one another between an opened position (FIGS. 1 and 2) and a closed position (FIGS. 11 and 12). A cutting member 106 is movably attached to the first jaw 102 so that the cutting member 106 extends from the first jaw 102 towards the second jaw 104. An actuating mechanism 108 is operably associated with the cutting member 106 so as to cause the cutting member 106 to move relative to the first jaw 102. More specifically, the surgical cutting tool 100 may include a first jaw part 112 including the first jaw 102 and a second jaw part 114 including the second jaw 104. The first jaw part 112 may further include a first jaw support member 116 and a handle 118. The second jaw part 104 may further include a second jaw support member 120 and a lever 122.

Figure 3:
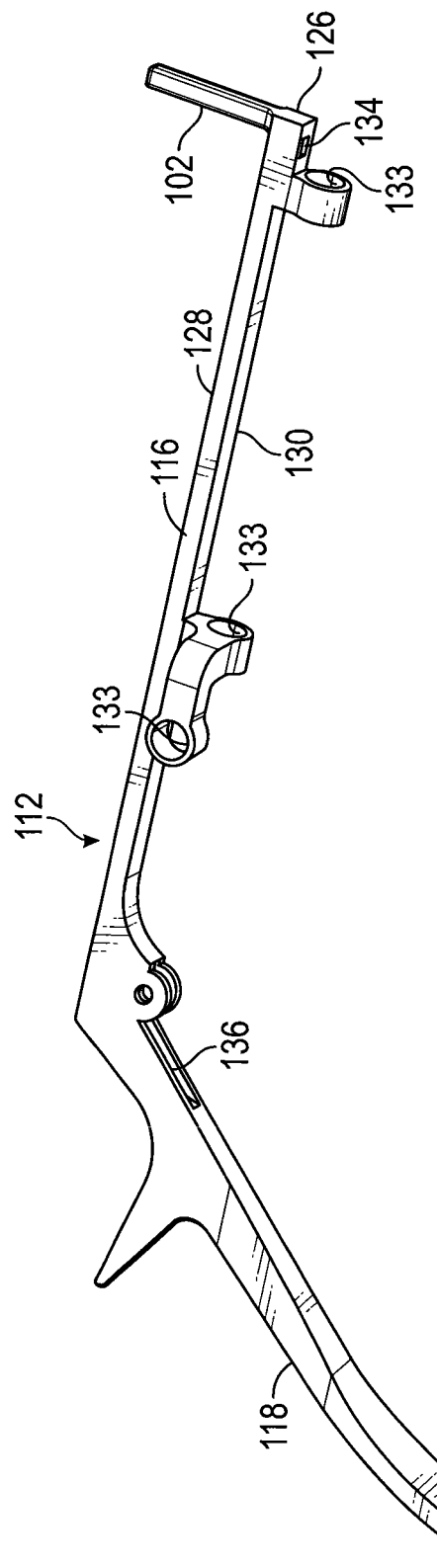
FIG. 3 is a bottom perspective view of a first jaw part of the surgical cutting tool of FIG. 1.
Figure 4:
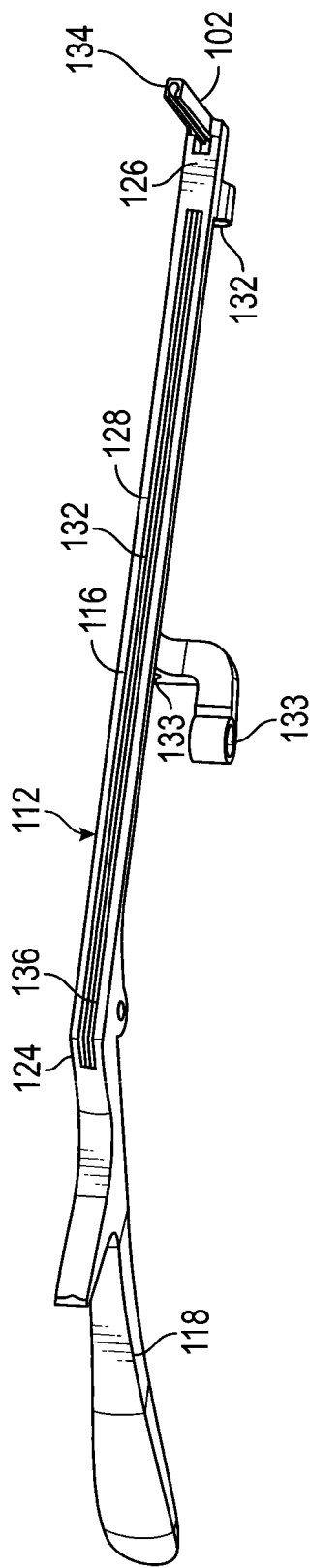
FIG. 4 is a top perspective view of the first jaw part of FIG. 3.

Referring now to FIGS. 3 and 4, the first jaw support member 116 may be a generally elongated member having a proximal end 124, a distal end 126, a first side 128, and a second side 130. The first side 128 may have one or more elongated connector features, such as a groove 132 (FIG. 4), formed therein. The groove 132 extends at least partially along the first side 128 and is configured to be slidably receive in a corresponding protrusion formed in the second jaw support member 120 such that the second jaw support member 120 may be slidably coupled to the first jaw support member 116, as will be described below.

One or more mounting rings 133 may extend from the second surface 118 and may be configured to allow the actuating mechanism 108 to attach to the first jaw structure member 116, for example. It is to be understood that the mounting rings 133 may be omitted in some exemplary embodiments of the inventive concepts disclosed herein, and the actuating mechanism 108 may be attached to the first jaw support member 116 in any suitable manner, such as via welds, crews, brackets, adhesives, seams, joints, and combinations thereof.

The handle 118 may be implemented as any structure configured to facilitate handling by a surgeon's hand, for example, and may include one or more retention features (not shown), such as knurls, grooves, roughened surfaces, striations, bumps, and combinations thereof. It is to be understood that in some exemplary embodiments of the inventive concepts disclosed herein, the handle 118 may be configured to be attached to a surgical robot arm (not shown).

The first jaw support member 116 and the handle 118 are further configured to receive the lever 122 for actuating the first jaw 102 relative to the second jaw 104. To this end, the first jaw support member 116 and the handle 118 may include a slot 136 configured to pivotally receive a portion of the lever 122 in a manner to be described in greater detail below.

In one embodiment, the first jaw 102 extends from the distal end 126 of the first jaw support member 116 in a substantially perpendicular relationship to the first jaw support member 116. However, it will be appreciated that the first jaw 102 may be arranged in a variety angles relative to the first jaw support member 116. Further, while the angle between the first jaw support member 116 and the first jaw 102 is shown as being fixed, some exemplary embodiments may include any suitable adjustable angle-mechanism (not shown) implemented between the first jaw support member 116 and the first jaw 102 such that the angle between first jaw support member 116 and the first jaw 102 may be adjusted as desired by surgeons, or as indicated by local patient anatomy.

The first jaw 102 is provided with a cutting member receiving channel 134 which extends longitudinally through the first jaw 102 and through the distal end 126 of the first jaw support member 116. The cutting member receiving channel 134 is configured to slidably receive and retain the cutting member 106 so that the cutting member 106 extends from the first jaw 102 towards the second jaw 104 and is moveable relative to the first jaw 102 in a reciprocating motion.

The first jaw 102 may be formed to have an atraumatic design so as to be substantially free of sharp edges or corners to avoid injuring to adjacent tissues as the surgical cutting tool 100 is used, for example. As illustrated herein, the distal end of the cutting member receiving channel 134 is open thereby facilitating replacement of the cutting member 106.

While the first jaw 102 and the first jaw support member 116 are shown and described as a unitary component, in some exemplary embodiments of the inventive concepts disclosed herein the first jaw 102 and the first jaw support member 116 may be implemented as separate components connected to one another, or may be made of different materials, as will be appreciated by a person of ordinary skill in the art. For example, a kit including a first jaw 102 having a first size or shape and another first jaw 102 having a second size or shape may be supplied to surgeons, allowing surgeons to select a jaw as indicated by the procedure or local patient anatomy, or as desired by the surgeon, and connect such first jaw to the first jaw support member 116, whether via a fixed-angle connection, or via an adjustable-angle connection.

Figure 5:
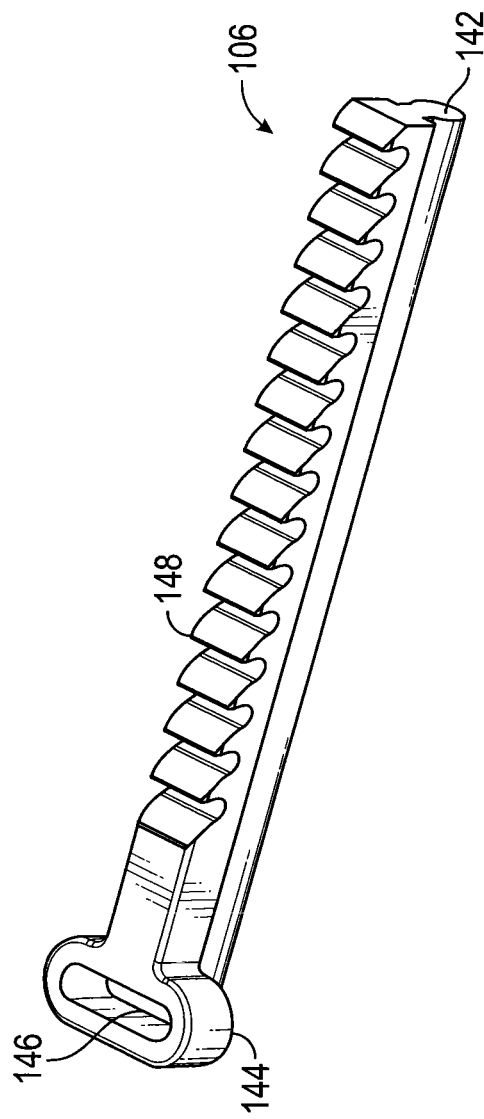
FIG. 5 is a perspective view of an exemplary embodiment of a cutting member.
Figure 6:
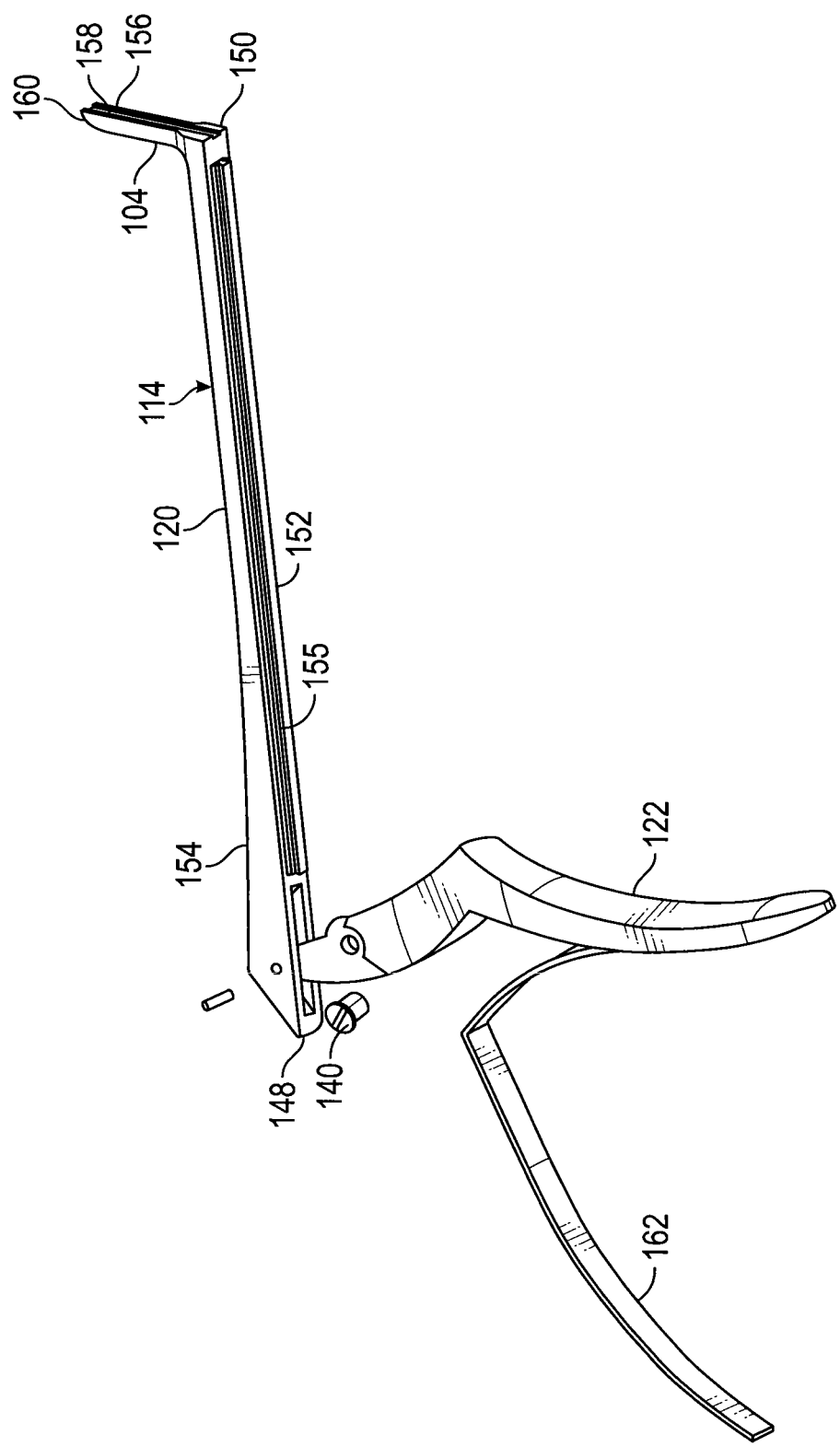
FIG. 6 is a perspective view of a second jaw part of the surgical cutting tool of FIG. 1 shown with a lever connected thereto.

Referring now to FIG. 5, the cutting member 106 may include a first end 142 and a second end 144 having a loop 146 formed therein, the loop 146 configured to receive a protrusion of the actuating mechanism 108 therein such that when the protrusion is rotated inside the loop 146, the cutting member 106 moves in a substantially reciprocating motion relative to the first jaw 102. The size of the loop 146 may be varied to vary a stroke length of the cutting member 106 as will be described below.

The cutting member 106 may be at least partially positionable in the cutting member channel 134 of the first jaw 102 and may be slidably movable relative to the first jaw 102. The cutting member 106 may have any desired cross-section corresponding to the cross-section of the cutting member receiving channel 134, such as substantially T-shaped, substantially C-shaped, substantially V-shaped, substantially triangular, substantially square, substantially rectangular, substantially oval, and combinations thereof, for example.

The cutting member 106 may be implemented as any suitable cutting member 106, such as a saw blade, a cutting wire, a scalpel blade, a serrated blade, and combinations thereof, for example. The cutting member 106 may include a plurality of teeth 148 configured to cut through bone and other tissues, for example. The teeth 148 may have any desired shape, size, and angle, and may be offset in some exemplary embodiments of the inventive concepts disclosed herein. For example, the teeth 148 may be unidirectional, or bi-directional, or may have a left or right offset, and combinations thereof. In some exemplary embodiments, the teeth 148 may be omitted, and a cutting blade may be implemented to cut through soft tissues, for example.

The cutting member 106 may be constructed of any suitable material, including surgical steel, titanium, titanium alloys, steel, alloys, ceramics, diamond, non-metals, resilient plastics, resins, glass, and combinations thereof, and may be coated with one or more hardening or abrasive materials, for example.

It is to be understood, however, that in some exemplary embodiments of the inventive concepts disclosed herein, the cutting member 106 may be implemented as a cutting wire (not shown) which may be looped through one or more pulleys (not shown) and connected to any suitable actuating mechanism capable of moving the cutting wire. For example, the cutting wire may be moved in a reciprocation path, or may be moved in a circular path, and combinations thereof as will be appreciated by a person of ordinary skill in the art.

Referring now to FIG. 5, the second jaw support member 120 may be a generally elongated member and have proximal end 148, a distal end 150, a first side 152, and a second side 154. The first side 152 may have one or more elongated connector features, such as a dovetail 155 (FIG. 5), formed thereon. The dovetail 155 extends at least partially along the first side 152 and is configured to be slidably received in the groove 132 of the first jaw support member 116 such that the second jaw support member 120 may be slidably coupled to the first jaw support member 116 so that the first and second jaw support member 116 and 120 move in a parallel relationship to one another (FIGS. 1 and 2). Further, in some exemplary embodiments, the second jaw support member 120 may be connected to the first jaw support member 116 in any suitable manner, such as via attachment loops, brackets, supports, bolts, screws, and combinations thereof, provided that the first and second jaw support members 116 and 120 may slide or otherwise move relative to one another.

The second jaw 104 extends from the distal end 150 of the second jaw support member 120 in a substantially perpendicular relationship to the second jaw support member 120 so as to be arranged in a substantially parallel relationship with respect to the first jaw 102. However, it will be appreciated that the second jaw 104 may be arranged in a variety angles relative to the second jaw support member 120. Further, like the first jaw 102, the angle between the second jaw support member 120 and the second jaw 104 may be fixed or be selectively adjustable.

The second jaw 104 is characterized as having a clamping surface 156. In one embodiment, the clamping surface 156 has a channel 158 formed therein configured to receive at least a portion of the cutting member 106 when the first jaw 102 and the second jaw 104 are in the closed position (FIG. 11).

The second jaw 104 may be formed to have an atraumatic design so as to be substantially free of sharp edges or corners to avoid injuring to adjacent tissues as the surgical cutting tool 100 is used. For example, a distal end 160 of the second jaw 104 may be tapered to facilitate insertion of the second jaw 104 between different tissues and structures.

Again, while the second jaw 104 and the second jaw support member 120 are shown and described as a unitary component, in some exemplary the second jaw 104 and the second jaw support member 120 may be implemented as separate components connected to one another, or may be made of different materials, as will be appreciated by a person of ordinary skill in the art. For example, a kit including a second jaw 104 having a first size or shape and another second jaw 104 having a second size or shape may be supplied to surgeons, allowing surgeons to select a jaw as indicated by the procedure or local patient anatomy, or as desired by the surgeon, and connect such second jaw to the second jaw support member 120, whether via a fixed-angle connection, or via an adjustable-angle connection.

The second jaw 104 is provided to serve as a brace for the cutting member 106 and to serve as a guard to protect nearby tissue from the cutting member 106. To this end, the second jaw 104 may be dimensioned to have a length at least as long as the length of the first jaw 102 and a width that is greater than the width of the cutting member 106 such that the cutting member 106 is substantially covered by the second jaw 106 when the first and second jaw 102 and 104 are in the closed position and the clamping surface 156 of the second jaw 104 may interface with the first jaw 102 and/or the cutting member 106 to clamp an object to be cut, such as a segment of bone or tissue and grasp the cut portion for removal from a patient's body.

The proximal end 148 of the second jaw support member 120 is configured to pivotally receive one end of the lever 122 (FIG. 1). The lever 122 is additionally extended through the slot 136 of the first jaw part 112 and is pivotally connected thereto via a pin 140. As will be appreciated by a person of ordinary skill in the art, the lever 122 may be operated, pivoted, or moved towards or away from the handle 118 to slide or otherwise move the second jaw 104 and the first jaw 102 relative to one such that the second jaw 104 may selectively interface with the first jaw 102.

A spring 162 may be connected with, or come into contact with handle 118 and the lever 122 such that the spring 162 biases or urges the lever 122 away from the handle 118, which in turn causes the second jaw 104 and the first jaw 102 to be biased in the opened position. It is to be understood that in some exemplary embodiments of the inventive concepts disclosed herein, the spring 162 may be omitted, or may be replaced with a latching mechanism (not shown) configured to latch and securely hold or clamp a tissue positioned between the second jaw 104 and the first jaw 102, for example.

Figure 7:
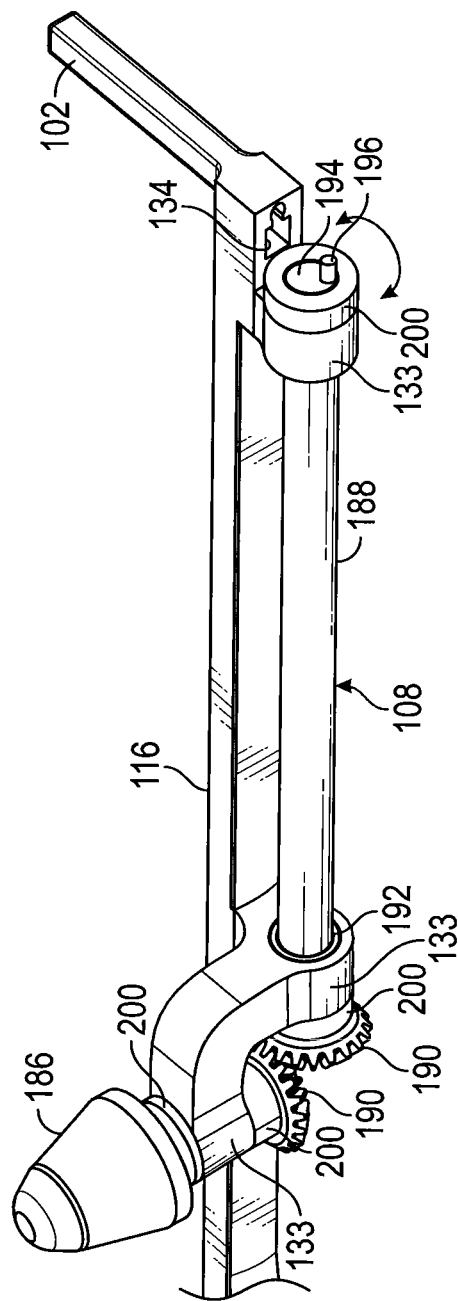
FIG. 7 is a perspective view of an actuator mechanism shown connected to the first jaw part with the cutting member removed from the first jaw part.

Referring now to FIG. 7, the actuator mechanism 108 may be mounted to the first jaw support member 116 and operatively coupled with the cutting member 106 so as to cause the cutting member 106 to move relative to the first jaw 102. The actuating mechanism 108 may be implemented as any suitable actuating mechanism 108 configured to move the cutting member 106, and may be manually, mechanically, or electrically powered, and combinations thereof, for example. The actuating mechanism 108 may include a knob 186 operably connected to a shaft 188 via meshing spiral bevel gears 190.

The shaft 188 may include a first end 192 connected to the gears 190, and a second end 194 having a protrusion 196 extending longitudinally therefrom. The protrusion 196 may extend radially from the second end 194 and may be configured and oriented such that the protrusion 196 moves in a substantially circular motion as the shaft 188 is rotated. As the knob 186 is rotated, the gears 190 transfer the rotational motion to the shaft 188, which rotates the shaft 188 and the protrusion 196 in a substantially circular motion as indicated by arrow 198, for example.

To operably couple the actuating mechanism 108 with the cutting member 106, the protrusion 196 may be inserted in the loop 146 of the cutting member 106, for example. As the protrusion 196 rotates in a circular motion and moves in the loop 146, it may operate in a cam-like fashion to convert the rotational motion of the shaft 188 into a reciprocating motion of the cutting member 106 in the first jaw 102, for example. To vary the stroke length of the cutting member 106, the size of the loop 146 or the location or size of the protrusion 196 of the shaft 188 may be varied, as will be readily appreciated by a person of ordinary skill in the art. For example, a first shaft 188 having a first protrusion 196 with a first size or first location, and a second shaft 188 having a second protrusion 196 with a second size or a second location may be provided with the surgical cutting tool 100 to allow surgeons to vary the stroke length of the cutting member 106 as indicated by a surgical procedure or as preferred by surgeons. As will be appreciated by a person of ordinary skill in the art, either direction of rotation (e.g., clockwise or counterclockwise) of the shaft 188 will result in the cutting member 106 reciprocating relative to the first jaw 102.

It is to be understood that the actuating mechanism 108 may be operatively coupled with the cutting member 106 in any suitable manner, provided that the actuating mechanism 108 is configured to move the cutting member 106 relative to the first jaw support member 116, for example. For example, one or more bushings 200 may be used to secure the actuating mechanism 108 to the first jaw support member 116 via the mounting rings 133. It is to be understood that in some exemplary embodiments of the inventive concepts disclosed herein, the actuating mechanism 108 may be movably connected to the first jaw support member 116 in any suitable manner, such as via brackets, welds, bearings, seams, joints, bolds, screws, adhesives, and combinations thereof.

The power to operate the actuating mechanism 108 may be provided manually, or by any suitable motive source such as a mechanical or electrical device or power source operatively coupled with the actuating mechanism 108, as will be appreciated by a person of ordinary skill in the art having the benefit of the instant disclosure.

It is to be understood that any suitable actuating mechanism 108 configured to move the cutting member 106 may be implemented with the inventive concepts disclosed herein, including a cutting wire spool mechanism, a crankshaft-and-piston-type of mechanism, a rack and pinion, a planet and gears, and combinations thereof, for example.

The surgical cutting tool 100 may be constructed of any suitable material, such as bioinert materials, surgical steel, titanium, titanium alloys, metals, alloys, thermoplastics, resins, plastics, ceramics, non-metals, and combinations thereof, for example. The surgical cutting tool 100 may be manufactured using any desired technique, such as casting, molding, machining, three-dimensional printing, and combinations thereof, for example.

Figure 8:
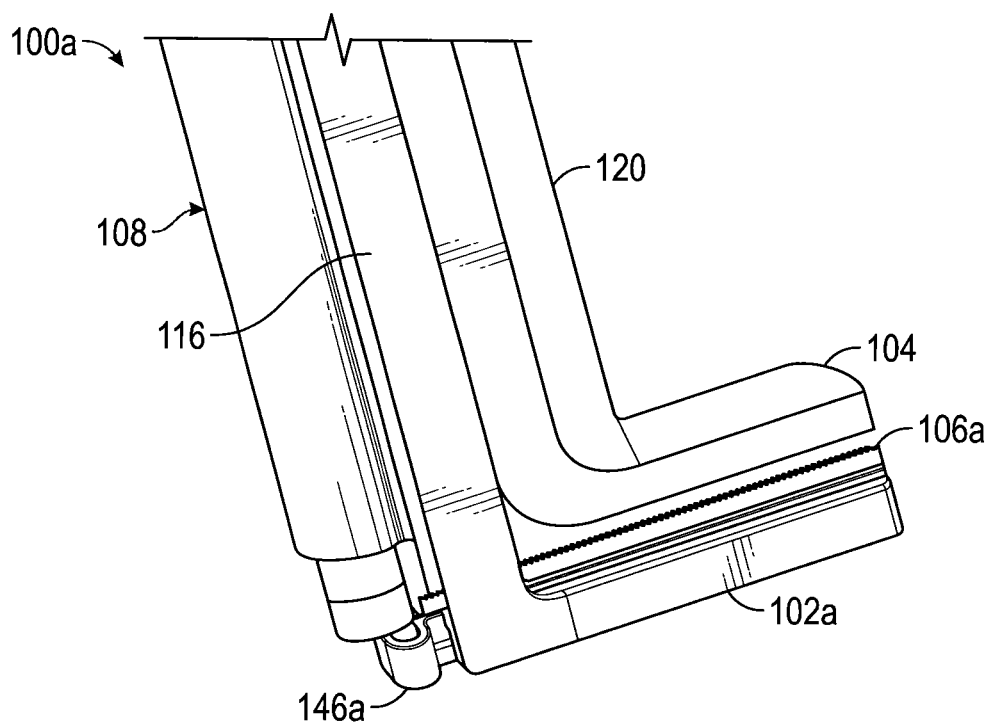
FIG. 8 is a perspective view of another embodiment of a surgical cutting tool constructed in accordance with the inventive concepts disclosed herein.
Figure 9:
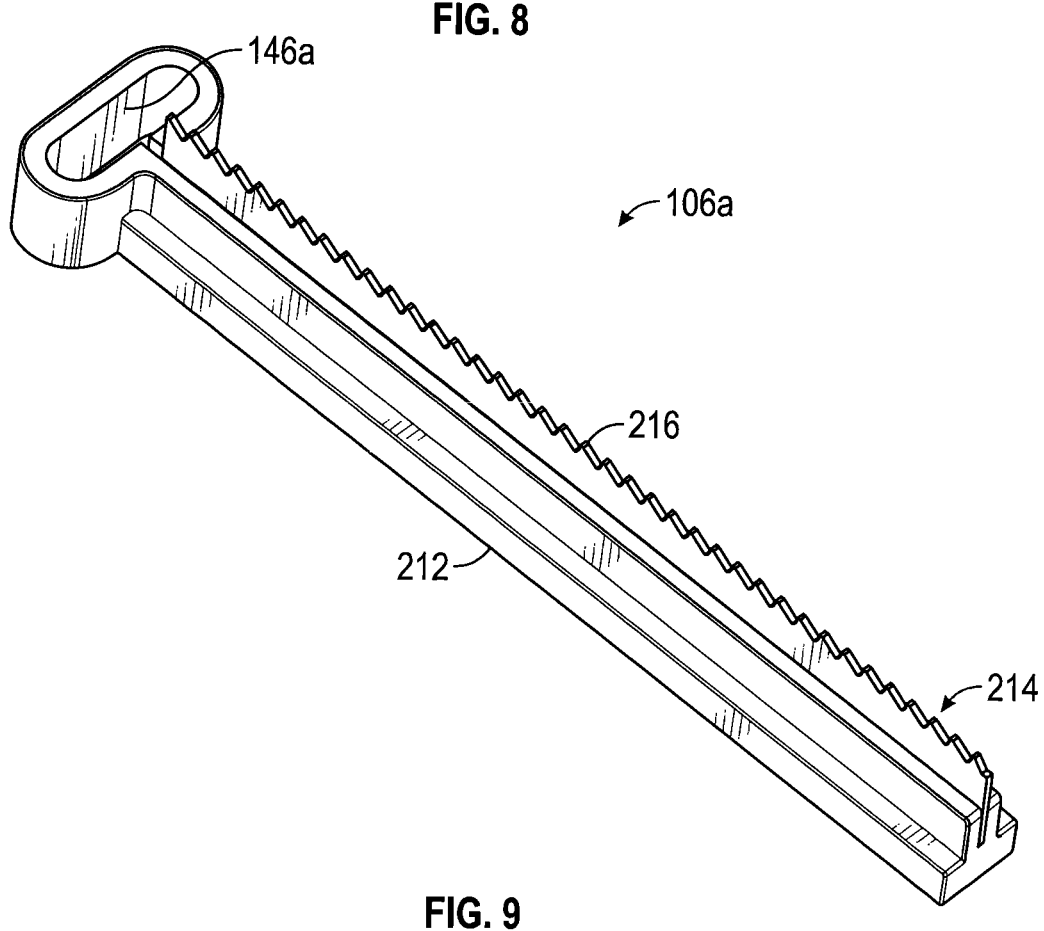
FIG. 9 is a perspective view of another embodiment of a cutting member.

Referring now to FIGS. 8 and 9, another embodiment of a surgical cutting tool 100a is illustrated. The surgical cutting tool 100a is similar in constructed to the surgical cutting tool 100 described above, except as described below. In particular, the surgical cutting tool 100a is provided with a cutting member 106a which is illustrated as including a base 212 and a blade 214 attached to the base 212, for example. The base 212 may have any desired cross-section and size, and desirably corresponds to the cross-section and size of a cutting member receiving channel 134a formed in the first jaw 102a. It is to be understood that while the base 212 and the cutting member receiving channel 134a are shown as being substantially T-shaped, the base 212 and the cutting member receiving channel 134a may have any desired cross-sections, such as circular, oval, rectangular, square, triangular, wedge-shaped, and combinations thereof, for example, to allow the base 212 to be slidably received by the connecting member receiving channel 134a.

The blade 214 may include a plurality of teeth 216 configured to cut through one or more tissues, for example. The teeth 216 may be unidirectional or bi-directional, and may have no offset or a left or a right offset, and combinations thereof, for example. In some exemplary embodiments, the teeth 216 may be omitted, and the blade 214 may have straight or arcuate cutting edge (not shown).

The blade 214 may be attached to the base 212 in any suitable manner, such as by being press-fitted into the base 212, or by being attached to the base 212 via adhesives, joints, welds, brackets, screws, and combinations thereof. In some exemplary embodiments the blade 214 may be permanently attached to the base 212, while in other exemplary embodiments the blade 214 may be removably attached to the base 212, such that the blade may be replaced as needed or desired by surgeons. Further, a kit including one or more blade 214 may be supplied with the surgical cutting tool 100a, allowing surgeons to select a blade 214 having any desired configuration of teeth 216, or having no teeth 216, for example.

Figure 10:
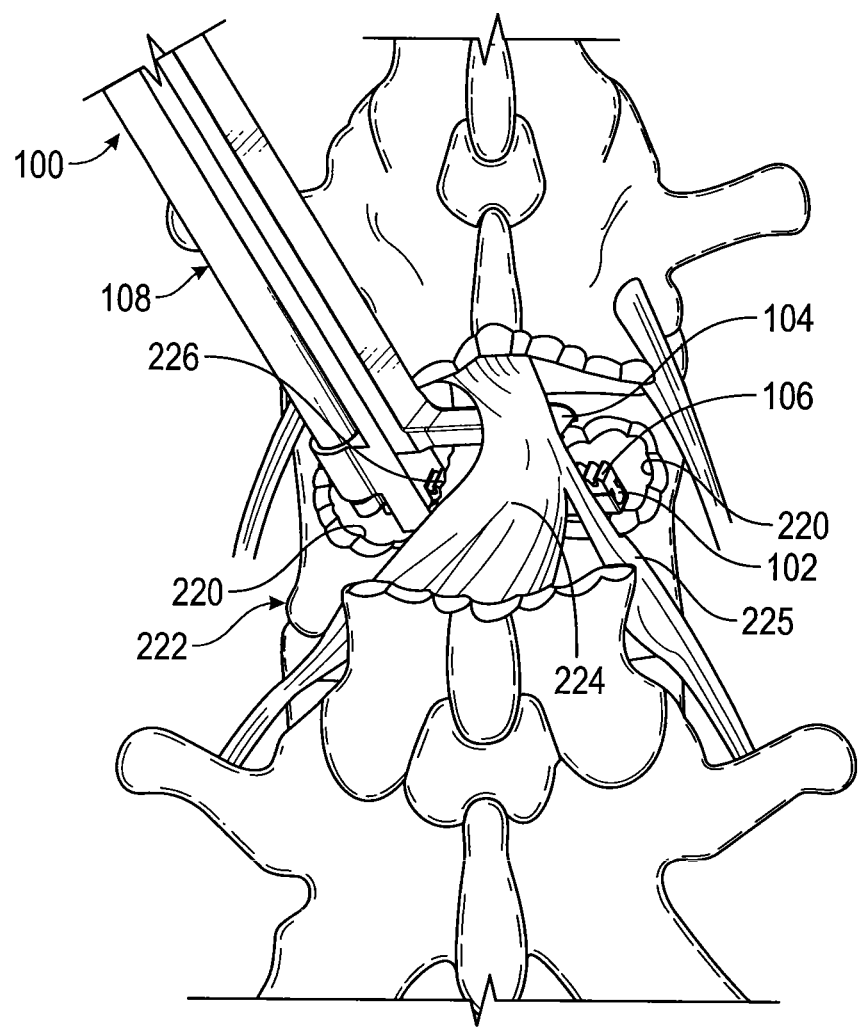
FIGS. 10-12 are diagrammatic views illustrating use of the surgical cutting tool.

Referring now to FIGS. 10-12, an exemplary embodiment of a method of cutting a posterior vertebral cortex or bone bridge in a PSO procedure with a surgical cutting tool 100 according to the inventive concepts disclosed herein is illustrated. The method may include the step of inserting the first jaw 102 of the surgical cutting tool 100 into one of two openings 220 created in a vertebral body 222 for decancellating the vertebral body 222 so that the cutting member 106 extends toward a posterior vertebral wall or bone bridge 226 of the vertebral body 222 (FIG. 10). The second jaw 104 is inserted on an opposing side of the bone bridge 226 of the vertebral body 222 between the bone bridge 226 and sensitive tissues, such as a spinal cord 224 and nerve roots, such as the nerve root 225. It will be appreciated that a posterior longitudinal ligament (not shown) may further be positioned between second jaw 104 and the bone bridge 226. With the first and second jaws 102 and 104 positioned, the actuating mechanism 108 is activated to cause the cutting member 106 to move relative to the first jaw 102. The first jaw 102 may then be caused to move relative to the second jaw 104 by operating the lever 152 (FIG. 1), for example, and thereby cause the cutting member 106 to cut through the bone bridge 226 and the posterior longitudinal ligament (FIG. 11). The steps may be repeated as necessary to detach the bone bridge 226 and the posterior longitudinal ligament spanning the two openings 220, for example.

The detached segment of the bone bridge 226 and the posterior longitudinal ligament may be extracted or removed via the surgical cutting tool 100 (FIG. 12), such as by angling the surgical cutting tool 100 and carefully sliding the second jaw 104 and the first jaw 102 away from the spinal cord 224 while maintaining clamping or compressive force between the second jaw 104 and the first jaw 102, for example. In some exemplary embodiments, substantially the entire bone bridge 226 may be extracted or removed as a single fragment, while in some exemplary embodiments the bone bridge 226 may be removed in two or more fragments as needed.

As will be appreciated by a person of ordinary skill in the art the steps of the method disclosed herein may be performed simultaneously or in any desired order, and may be carried out by a human, or by a machine (e.g., a surgical robot), and combinations thereof, for example. For example, one or more of the steps of the method disclosed herein may be omitted, one or more steps may be further divided in one or more sub-steps, and two or more steps or sub-steps may be combined in a single step, for example. Further, in some exemplary embodiments, one or more steps may be repeated one or more times, whether such repetition is carried out sequentially or interspersed by other steps or sub-steps. Additionally, one or more other steps or sub-steps may be carried out before, after, or between the steps disclosed herein, for example.

It is to be noted that, while the inventive concepts disclosed herein have been described in connection with a pedicle subtraction osteotomy procedures and methods, surgical cutting tools and methods according to the instant inventive concepts are not limited to being used in pedicle subtraction osteotomies, and may be implemented in any surgical procedure where one or more tissues are cut, and where there is potential for injuries to an adjacent tissue, for example. Exemplary embodiments of the inventive concepts disclosed herein may be implemented in a variety of surgical or veterinary procedures as will be readily recognized by persons or ordinary skill in the art and the instant inventive concepts are intended to encompass such embodiments and implementations, for example.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished within the scope of the inventive concepts disclosed and as defined in the appended claims.

What is claimed is:

1. A method, comprising:
   positioning a first jaw on one side of at least one tissue of a patient, the first jaw extending transversely from a first jaw support member;
   positioning a second jaw on an opposing side of the at least one tissue, the second jaw extending transversely from a second jaw support member, the first jaw support member and the second jaw support member slidably coupled together;
   sliding the first jaw support member relative to the second jaw support member thereby causing the first jaw and the second jaw to move more proximate each other on opposing sides of the at least one tissue;
   actuating a cutting member mounted to the first jaw so that the cutting member moves in a reciprocating manner relative to the first jaw so as to cause the cutting member to cut the at least one tissue.

2. The method of claim 1, wherein the tissue is at least a bone bridge positioned at a posterior aspect of a vertebra of the patient and created by forming at least one hole in the vertebra and decancellating at least a portion of the vertebra, and wherein the method further comprises the steps of:
   inserting the first jaw in the opening of the vertebra with the cutting member extending toward the bone bridge; and
   positioning the second jaw between the bone bridge and at least one of a spinal cord and a nerve root of the patient.

3. The method of claim 2, wherein the tissue is further a posterior longitudinal ligament of the patient, and wherein the step of positioning the second jaw between the bone bridge and the at least one of the spinal cord and the nerve root, further comprises positioning the second jaw between the posterior longitudinal ligament of the patient and at least one of the spinal cord and the nerve root of the patient.

4. The method of claim 2, further comprising the steps of:
   positioning the first jaw on one side of another portion of the bone bridge;
   positioning the second jaw on an opposite side of the bone bridge relative to the first jaw between the bone bridge and at least one of the spinal cord and the nerve root;
   actuating the cutting member relative to the first jaw so that the cutting member moves relative to the first jaw.

5. The method of claim 4, further comprising the step of:
   clamping the detached bone segment between the first jaw and the second jaw; and
   removing the detached bone segment from the patient.

6. The method of claim 4, wherein the step of positioning the second jaw between the bone bridge and the at least one of the spinal cord and the nerve root, further comprises positioning the second jaw between the posterior longitudinal ligament of the patient and at least one of the spinal cord and the nerve root of the patient so that the cutting member is caused to cut through the posterior longitudinal ligament to define a detached ligament segment.

7. The method of claim 6, further comprising the step of:
   clamping the detached bone segment and the detached ligament segment between the first jaw and the second jaw; and
   removing the detached bone segment and the detached ligament section from the patient.

* * * * *